(12) United States Patent
Turos et al.

(10) Patent No.: US 7,482,467 B2
(45) Date of Patent: Jan. 27, 2009

(54) N-THIOLATED 2-OXAZOLIDINONE-DERIVED ANTIBIOTICS

(75) Inventors: Edward Turos, Tampa, FL (US); Rajesh Kumar Mishra, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 11/948,073

(22) Filed: Nov. 30, 2007

(65) Prior Publication Data

US 2008/0119533 A1    May 22, 2008

Related U.S. Application Data

(62) Division of application No. 11/382,157, filed on May 8, 2006, now Pat. No. 7,332,611.

(60) Provisional application No. 60/678,292, filed on May 6, 2005.

(51) Int. Cl.
*C07D 263/02* (2006.01)

(52) U.S. Cl. .................. 548/230; 548/229; 514/376

(58) Field of Classification Search ............ None
See application file for complete search history.

(56) References Cited

U.S. PATENT DOCUMENTS 4,451,475 A    5/1984  Busse et al.
6,476,015 B1  11/2002  Turos et al.
6,946,458 B2   9/2005  Turos
7,332,611 B2   2/2008  Turos et al.

OTHER PUBLICATIONS

Chopra, I.; Hodgson, J.; Metcalf, B.; Poste, G. 1997. The Search for Antimicrobial Agents Effective Against Bacteria Resistant to Multiple Antibiotics. Antimicrobial Agents and Chemotherapy. 41: 497-503.

Evans, D.A.; Faul, M.M.; Colombo, L.; Bisaha, J.J.; Clardy, J.; Cherry, D. 1992. Asymmetric Synthesis of Chiral Organosulfur Compounds Using N-Sulfinyloxazolidinones. J. Am. Chem. Soc. 114: 5977-5985.

Mishra, R.K.; Revell, K.D.; Coats, C.M.; Turos, E.; Dickey, S.; Lim, D.V. 2006. N-thiolated 2-oxazolidinones: A new family of antibacterial agents for methicillin-resistant *Staphylococcus aureus* and *Bacillus anthracis*. Bioorganic & Medicinal Chemistry Letters. 16: 2081-2083.

*Primary Examiner*—Kamal A Saeed
*Assistant Examiner*—Sun Jae Y Loewe
(74) *Attorney, Agent, or Firm*—Anton J. Hopen; Smith & Hopen, P.A.

(57) ABSTRACT

This invention describes the discovery and synthesis of N-thiolated 2-oxazolidinones as a new class of anti bacterial agents. These compounds can be synthesized from 2-oxazolidinones by Ndeprotection and N-sulfenylation. These new substances were found to exhibit potent anti-bacterial activity, including bacteriostatic properties against *Staphylococcus* spp., including methicillin resistant *Staphylococcus aureus* (MRSA), and *Bacillus* spp., including *Bacillus anthracis*.

13 Claims, 2 Drawing Sheets

(A)  (B)

N-THIOLATED 2-OXAZOLIDINONE-DERIVED ANTIBIOTICS

CROSS REFERENCE TO RELATED APPLICATIONS

This application is a divisional of pending U.S. Nonprovisional patent application Ser. No. 11/382,157, entitled "N-Thiolated 2-Oxazolidinone Antibiotics", filed May 8, 2006, which claims priority to U.S. Provisional Patent Application 60/678,292, entitled, "N-Thiolated 2-Oxazolidinones: A New Class of Anti-bacterial Drug", filed May 6, 2005, the contents of which are herein incorporated by reference.

STATEMENT OF GOVERNMENT INTEREST

This invention was made with Government support under Grant No. R01 AI 51351 awarded by the National Institutes of Health. The Government has certain rights in the invention.

FIELD OF INVENTION

This invention pertains to the synthesis and characterization of a new family of antibacterial drug. More specifically this invention relates to N-thiolated 2-oxazolidinones as a new class of synthetic antibacterial agents.

BACKGROUND OF THE INVENTION

The clinical use of antibiotics in the 20th century has substantially decreased morbidity from bacterial infections. The early success of penicillin was extended by various sulfonamide drugs developed in the 1930s, and subsequently by a "golden" period of discovery, between 1945 and 1970, during which a wide array of highly effective agents are discovered and developed (Chopra, I., et al., "The Search for Antimicrobial Agents Effective against Bacteria Resistant to Multiple Antibiotics" *Antimicrobial Agents and Chemotherapy*, 1997, 41:497-503).

However, since the 1980s the introduction of new antibiotics has slowed, and, concurrently, there has been an alarming increase in bacterial resistance to existing agents that now constitutes a serious threat to public health (Brown, A. G. "Discovery and Development of New β-Lactam Antibiotics" *Pure & Appl. Chem.*, 1987, 59:475-484). Hospitals, nursing homes and infant day care centers have become breeding grounds for the most tenacious drug-resistant pathogens ("Frontiers in Biotechnology" *Science*, 1994, 264:359-393). There has been an alarming rise in drug resistant *staphylococci*, *enterococci*, *streptococci*, and *pneumococci* infections, and a rise in tuberculosis, influenza and sepsis.

The problem of bacterial drug resistance has reached a crisis level such that successful treatment of antibiotic-resistant infections in hospitals and health care centers can no longer be taken for granted. Infections caused by methicillin-resistant *Staphylococcus aureus* (MRSA) are becoming particularly difficult to treat with conventional antibiotics such as penicillin, leading to a sharp rise in clinical complications and deaths. The need for new antibacterial agents and protocols for treating MRSA infections is becoming extremely serious.

A novel family of lipophilic N-thiolated β-lactams that are effective growth inhibitors of MRSA and *Bacillus* species has been reported (U.S. Pat. No. 6,473,015 B1 to Turos et al. and U.S. Pat. No. 6,946,458 B2 to Turos; see also. Ren, X. F. et al., *J. Org. Chem.* 60 (1995), p. 4980; Ren, X. F. et al., *J. Org. Chem.* 63 (1998), p. 8898; E. Turos, E. et al., *Tetrahedron* 56 (2000), p. 5571; E. Turos, E. et al., *Bioorg. Med. Chem. Lett.* 12 (2002), p. 2229; C. Coates, C. et al., *Bioorg. Med. Chem.* 11 (2003), p. 193; Long, E. et al., *Bioorg. Med. Chem.* 11 (2003), p. 1859; Kazi, A. et al., *Biochem. Pharmacol.* 67 (2004), p. 365; Turos, E. et al., *J. Bioorg. Med. Chem. Lett.* 2006 (in press)). The mode of action and structure-activity profiles differ dramatically from those of traditional β-lactams. (See generally *Chemistry and Biology of β-Lactam Antibiotics*; Morin, R. B., Gorman, M.; Eds.; Academic Press: New York, 1982; Vols 1-3.) Investigations have shown that these β-lactam compounds can carry a wide range of substituents at the $C_3$ and $C_4$ centers; however, the N-organothio substituent is necessary for microbiological activity. (E. Turos, E. et al., *Bioorg. Med. Chem.* 13 (2005), p. 6289.) The mechanism of action is under investigation but appears to depend on the ability of the compounds to transfer the organothio moiety onto a cellular thiol. This suggests that the role of the lactam ring is to provide a structural framework for the delivery of the thiol moiety and may not be absolutely required for the activity. To probe this possibility, and to expand on the structural diversity of anti-MRSA compounds available for clinical development, oxazolidinones were examined as potential antibacterially active organothio carriers. Oxazolidinones are already recognized for their favorable pharmacological properties and are the only new class of antibacterial drugs introduced into clinical use in the last three decades. (Brickner, S., *J. Curr. Pharm. Des.* 2 (1996), p. 175; Phillips, O. A., *Curr. Opin. Invest. Drugs* 4 (2003), p. 117; S. J. Brickner, S. J. et al., *J. Med. Chem.* 39 (1996), p. 673.)

Infections caused by methicillin-resistant *Staphylococcus aureus* (MRSA) are becoming extremely difficult to treat with conventional antibiotics, leading to a sharp rise in clinical complications (Binder, S. et al. *Science*, 1999, 284:1311). The need for new antibiotics and protocols for treating MRSA infections is extremely serious.

There is a clear need for new antibacterial agents to combat pathogenic bacteria that have become resistant to current antibiotics. Towards this end, a novel class of derivatized, N-thiolated-2-Oxazolidinones have been developed in the present invention, that exhibit strong antibacterial activity against a wide variety of species and strains, including methicillin-resistant *Staphylococcus aureus*.

SUMMARY OF INVENTION

This invention pertains to the synthesis of a new family of antibacterial drug. N-thiolated-2-Oxazolidinones represent a new class of antibacterial agent for methicillin-resistant *Staphylococcus aureus*. Described herein is the synthesis and application of N-thiolated 2-oxazolidinones as a new class of anti bacterial agents. These compounds can be synthesized from 2-oxazolidinones by N-deprotection and N-sulfenylation. These new substances were found to exhibit potent anti-bacterial activity, including bacteriostatic properties against methicillin resistant *Staphylococcus aureus* (MRSA).

The general structure of these N-thiolated 2-oxazolidinones is:

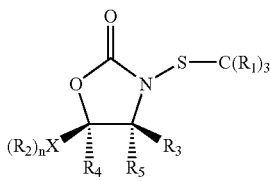

wherein $R_{1-5}$ are independently hydrogen, alkyl, heteroalkyl, aryl, heteroaryl, alkenyl, or alkynyl; X is H, C or O; and n=0 to 3.

It is an object of the present invention to provide these compounds, including their salts, hydrates, and in combinations with suitable pharmaceutical carriers, as antibacterial and antibiotic agents.

It is a further object of this invention to provide such compounds, wherein $R_4$ and $R_5$ are hydrogen, and —$C(R_1)_3$ is aryl or heteroaryl.

It is a further object of this invention to provide antibacterial and antibiotic agents with varying bacterial strain specificities and efficacies, by the expedient means of varying substituents of the 2-oxazolidinone ring, including but not limited to nitrogen (N-1) methylthio or benzylthio moieties, and substitutions at the $C_3$ and $C_4$ positions.

In certain embodiments the present invention provides methods for inhibiting the growth of bacteria by administering the compounds of the present invention, and to provide methods for the treatment of bacterial infections of a patient, in which one or more doses of an effective amount of the compounds and compositions of the present invention are administered to a patient.

The present invention provides a method of inhibiting a bacterial infection comprising administering an effective amount of the N-thiolated 2-oxazolidinone of claim 1, to a patient in need thereof.

In certain embodiments the bacterium is a *Staphylococcus* spp. In certain specific embodiments the *Staphylococcus* spp. is a methicillin-resistant *Staphylococcus*. In still further embodiments the methicillin-resistant *Staphylococcus* can be MRSA USF919, MRSA USF920, MRSA USF652, MRSA USF653, MRSA USF654, MRSA USF655, MRSA USF656, MRSA USF657, MRSA USF658 or MRSA USF659.

In certain embodiments the bacterium is a *Bacillus* spp. In still further embodiments the *Bacillus* spp. can be *B. anthracis*, *B. globigii*, *B. thurigensis*, *B. megaterium*, *B. subtilis*, *B. cereus* and *B. coagulans*.

In certain embodiments the present invention provides compounds and compositions suitable for the treatment of *Staphylococcus* spp. infection.

In certain embodiments the present invention provides a method of inhibiting *Staphylococcus* spp. infection. In further embodiments the present invention provides a method of inhibiting methicillin-resistant *Staphylococcus aureus* infection.

In certain embodiments the present invention provides compounds and compositions suitable for the treatment of *Bacillus* spp. infection.

In certain embodiments the present invention provides a method of inhibiting *Bacillus* spp. infection. In further embodiments the present invention provides a method of inhibiting methicillin-resistant *Staphylococcus aureus* infection.

It is a further object of this invention to provide a mechanism of inhibiting infection comprising administering an N-thiolated 2-oxazolidinone antibacterial compound to a patient in need thereof, where said antibacterial compound affects events within the cytoplasm of the cell.

It is a further object of this invention to provide a mechanism of inhibiting bacterial infection by a means other than inhibiting cell wall cross-linking.

It is a further object of this invention to provide a mechanism of inhibiting bacterial infection through the use of an antibacterial compound that does not block bacterial cell growth by inhibiting penicillin binding proteins.

The present invention confers numerous advantages over the compounds of the prior art, including the following: ease of synthesis, whereby compounds with diverse substitutents may be synthesized and tested for antibacterial and antibiotic activity; the invention provides novel antibacterial and antibiotic agents to which bacterial pathogens have not yet acquired resistance; and the invention provides novel compounds for the treatment of increasingly common and resistant diseases. Surprisingly, the inventors have found that antibacterial and antibiotic activities can be obtained in compounds that do not possess traditional activating groups attached to the nitrogen, as required for activity in conventional monobactams which contain, for example, a sulfonic acid group. The inventors have also surprisingly discovered that derivatization of structure (A) in FIG. 1 at the positions indicated by the $R_{1-5}$ and X, results in compounds exhibiting different specificities for different bacterial pathogens, in a manner that is currently not possible to predict a priori. This aspect is therefore an unobvious benefit of the present invention. The present invention fulfills an urgent need in that novel compounds are urgently required as bacterial pathogens increasingly acquire immunity towards the present arsenal of antibiotics.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

This invention pertains to the synthesis of a new family of antibacterial drug. N-thiolated-2-Oxazolidinones represent a new class of antibacterial agent for methicillin-resistant *Staphylococcus aureus*. Described herein is the synthesis and application of N-thiolated 2-oxazolidinones as a new class of anti bacterial agents. These compounds can be synthesized from 2-oxazolidinones by N-deprotection and N-sulfenylation. These new substances were found to exhibit potent anti-bacterial activity, including bacteriostatic properties against methicillin resistant *Staphylococcus aureus* (MRSA).

Figure 1:
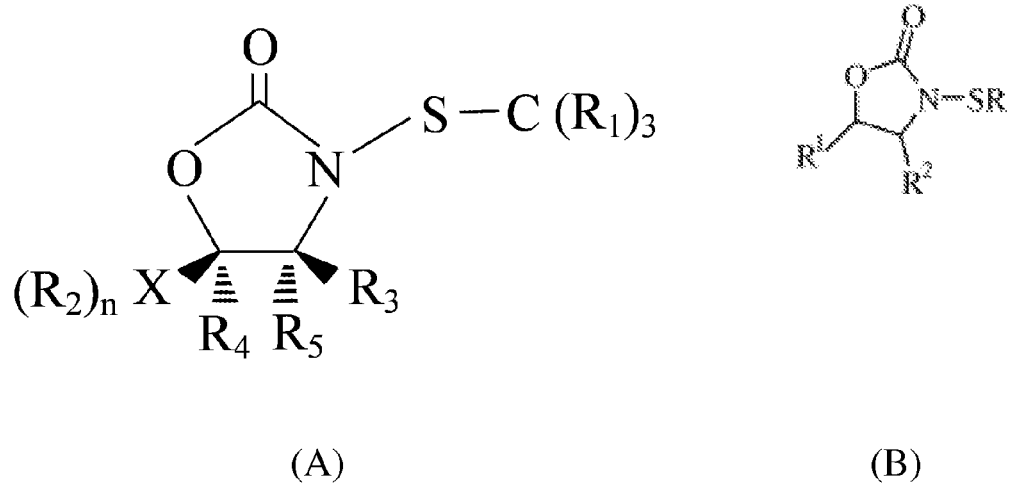
FIG. 1 shows an N-methylthio 2-oxazolidinone.

The term "N-thiolated-2-Oxazolidinones" is used herein to refer to a cyclic 5-membered compound comprising a 2-Oxazolidinone ring in which the ring nitrogen (N-1) atom is covalently bonded to a sulfur that is covalently bonded to a carbon-centered moiety, and which may be further modified as described herein. Specifically, referring now to compound (A) as shown in FIG. 1, X may be a hydrogen (in which case, n is preferably zero), or a carbon atom (in which case, n is preferably 3), or an oxygen atom (in which case, n is preferably 1), and $R_2$ may be any substituent as herein defined. Similarly, $R_1$ and $R_{3-5}$ may be independently any substituent as herein defined.

Thus, in advantageous embodiments, $R_1$ is hydrogen or benzyl, and in particularly advantageous embodiments $R_1$ is hydrogen. Substituents comprising $-X(R_2)_n$ are preferably methoxy and hydrogen, and most preferably methoxy. $R_3$ may be alkyl, heteroalkyl, aryl, heteroaryl, alkenyl, or alkynyl. Preferred $R_3$ substituents are phenylethynyl, acetoxy, 1-propenyl, ortho-chlorophenyl, ortho-nitrophenyl, 2-thiophene, or S,S-dioxo-thiophene. $R_4$ and $R_5$ may be independently alkyl, heteroalkyl, aryl, heteroaryl, alkenyl, or alkynyl groups. In preferred embodiments, $R_4$ and $R_5$ are H.

The following definitions are used, unless otherwise described. Halo is fluoro, chloro, bromo, or iodo. "Alkyl," "alkoxy," etc. denote both straight and branched groups; but reference to an individual radical such as "propyl" embraces only the straight chain radical, a branched chain isomer such as "isopropyl" being specifically referred to. "Aryl" denotes a phenyl radical or an ortho-fused bicyclic carbocyclic radical having about nine to ten ring atoms in which at least one ring is aromatic. "Heteroaryl" encompasses a radical attached via a ring carbon of a monocyclic aromatic ring containing five or six ring atoms consisting of carbon and one to four heteroatoms each selected from the group consisting of non-peroxide oxygen, sulfur, and $N(R_x)$ wherein $R_x$ is absent or is hydrogen, oxo, alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. "Heteroalkyl" encompasses the replacement of a carbon atom within an alkyl chain with a heteroatom; e.g., replacement with an element other than carbon such as N, S, or O, including both an alkyl interrupted by a heteroatom as well as an alkyl substituted by a heteroatom.

It will be appreciated by those skilled in the art that compounds of the invention having one or more chiral center(s) may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis, from optically-active starting materials, by chiral synthesis, or by chromatographic separation using a chiral stationary phase), and how to determine antibacterial activity using the tests described herein, or using other tests which are well known in the art.

Specific and preferred values listed below for radicals, substituents, and ranges, are for illustration only; they do not exclude other defined values or other values within defined ranges for the radicals and substituents.

Specifically, "alkyl" can include methyl, ethyl, propyl, isopropyl, butyl, iso-butyl, sec-butyl, pentyl, 3-pentyl, hexyl, heptyl, octyl, nonyl, decyl, undecyl, dodecyl, tridecyl, tetradecyl or pentadecyl; "alkenyl" can include vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl; 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, 11-dodecenyl, 1-tridecenyl, 2-tridecenyl, 3-tridecenyl, 4-tridecenyl, 5-tridecenyl, 6-tridecenyl, 7-tridecenyl, 8-tridecenyl, 9-tridecenyl, 10-tridecenyl, 11-tridecenyl, 12-tridecenyl, 1-tetradecenyl, 2-tetradecenyl, 3-tetradecenyl, 4-tetradecenyl, 5-tetradecenyl, 6-tetradecenyl, 7-tetradecenyl, 8-tetradecenyl, 9-tetradecenyl, 10-tetradecenyl, 11-tetradecenyl, 12-tetradecenyl, 13-tetradeceny, 1-pentadecenyl, 2-pentadecenyl, 3-pentadecenyl, 4-pentadecenyl, 5-pentadecenyl, 6-pentadecenyl, 7-pentadecenyl, 8-pentadecenyl, 9-pentadecenyl, 10-pentadecenyl, 11-pentadecenyl, 12-pentadecenyl, 13-pentadecenyl, 14-pentadecenyl; "alkoxy" can include methoxy, ethoxy, propoxy, isopropoxy, butoxy, iso-butoxy, sec-butoxy, pentoxy, 3-pentoxy, hexoxy, heptyloxy, octyloxy, nonyloxy, decyloxy, undecyloxy, dodecyloxy, tridecyloxy, tetradecyloxy, or pentadecyloxy; "alkanoyl" can include acetyl, propanoyl, butanoyl, pentanoyl, hexanoyl, heptanoyl, octanoyl, nonanoyl, decanoyl, undecanoyl, dodecanoyl, tridecanoyl, tetradecanoyl, or pentadecanoyl; "cycloalkyl" can include cyclopropyl, cyclobutyl, cyclopentyl, cyclohexyl, cycloheptyl, or cyclooctyl. "Aryl" can include phenyl, indenyl, 5,6,7,8-tetrahydronaphthyl, or naphthyl. "Heteroaryl" can include furyl, imidazolyl, tetrazolyl, pyridyl, (or its N-oxide), thienyl, pyrimidinyl (or its N-oxide), indolyl, or quinolyl (or its N-oxide).

Specific independent values for $R_{1-5}$, include alkyl, alkenyl, alkynyl, cycloalkyl, cycloalkyl($C_1$-$C_{10}$)alkyl, ($C_3$-$C_8$)cycloalkyl($C_1$-$C_{15}$)alkenyl, ($C_3$-$C_8$)cycloalkyl($C_1$-$C_{15}$)alkynyl, ($C_1$-$C_{15}$)alkoxy, ($C_1$-$C_{15}$)alkanoyl, or ($C_1$-$C_{15}$)alkanoyloxy; wherein $R^1$ is optionally substituted with one or more (e.g., 1, 2, 3, or 4) substituents independently selected from the group consisting of halo, nitro, cyano, hydroxy, trifluoromethyl, trifluoromethoxy, ($C_1$-$C_{15}$)alkyl, ($C_2$-$C_{15}$)alkenyl, ($C_2$-$C_{15}$)alkynyl, ($C_3$-$C_8$)cycloalkyl, ($C_3$-$C_8$)cycloalkyl, ($C_1$-$C_{15}$)alkyl, ($C_3$-$C_8$)cycloalkyl-($C_2$-$C_{15}$)alkenyl, ($C_3$-$C_8$)cycloalkyl($C_2$-$C_{15}$)alkynyl, ($C_1$-$C_{15}$)alkoxy, ($C_1$-$C_{15}$)alkanoyl, ($C_1$-$C_{15}$)alkanoyloxy, $C(=O)OR_a$, $C(=O)NR_bR_c$, $OC(=O)OR_a$, $OC(=O)NR_bR_c$, AND $NR_eR_f$.

Other specific values for $R_{1-5}$ include aryl optionally substituted with 1, 2, or 3 substituents independently selected from the group consisting of halo, nitro, cyano, hydroxy, trifluoromethyl, trifluoromethoxy, ($C_1$-$C_6$)alkyl, ($C_2$-$C_{10}$)alkenyl, ($C_2$-$C_{10}$)alkynyl, ($C_3$-$C_8$)cycloalkyl, ($C_3$-$C_8$)cycloalkyl, ($C_1$-$C_6$)alkyl, ($C_1$-$C_{10}$)alkoxy, ($C_1$-$C_{10}$)alkanoyl, ($C_2$-$C_{10}$)alkanoyloxy, $C(=O)OR_a$, $C(=O)NR_bR_c$, or $NR_eR_f$.

Other specific values for $R_{1-5}$, include independently phenyl or naphthyl, optionally substituted with a substituent selected from the group consisting of halo, nitro, cyano, hydroxy, trifluoromethyl, trifluoromethoxy, ($C_1$-$C_6$)alkyl, ($C_2$-$C_{10}$)alkenyl, ($C_2$-$C_{10}$)alkynyl, ($C_3$-$C_8$)cycloalkyl, ($C_3$-$C_8$)cycloalkyl($C_1$-$C_6$)alkyl, ($C_1$-$C_{10}$)alkoxy, ($C_1$-$C_{10}$)alkanoyl, ($C_2$-$C_{10}$)alkanoyloxy, $C(=O)OR_a$, $C(=O)NR_bR_c$, or $NR_eR_f$.

Still other specific values for $R_{1-5}$, include aryl, heteroaryl, aryl($C_1$-$C_6$)alkyl, heteroaryl($C_1$-$C_6$)alkyl, aryl($C_2$-$C_6$)alkenyl, heteroaryl($C_2$-$C_6$)alkenyl, aryl($C_2$-$C_6$)alkynyl, or heteroaryl($C_2$-$C_6$)alkynyl; wherein any aryl or heteroaryl is optionally substituted with halo, nitro, cyano, hydroxy, trifluoromethyl, trifluoromethoxy, ($C_1$-$C_{15}$)alkyl, ($C_2$-$C_{15}$)alkenyl, ($C_2$-$C_{15}$)alkynyl, ($C_3$-$C_8$)cycloalkyl, ($C_3$-$C_8$)cycloalkyl($C_1$-$C_{15}$)alkyl, ($C_3$-$C_8$)cycloalkyl-($C_2$-$C_{15}$)alkenyl, ($C_3$-$C_8$)

cycloalkyl($C_2$-$C_{15}$)alkynyl, ($C_1$-$C_{15}$)alkoxy, ($C_1$-$C_{15}$) alkanoyl, ($C_1$-$C_{15}$)alkanoyloxy, C(=O)O$R_a$, C(=O)N$R_b R_c$, or N$R_e R_f$.

The compounds of the present invention exhibit broad antibacterial activity against several families of bacteria in the Gram-negative and Gram-positive range, and against beta-lactamase formers. Because of their powerful antibacterial properties, the present compounds may also be used to supplement feed for animals.

In addition, the compounds of the present invention that exhibit antibacterial activity may also be used as medicaments, and also as substances for preserving inorganic and organic materials, especially organic materials of all kinds, for example, polymers, lubricants, paints, fibers, leather, paper, timber, foodstuffs, and water. For example, these compounds can be covalently bonded to the polymer.

The compounds of the present invention may also be used to prevent, alleviate, or cure diseases caused by pathogens whose growth is inhibited by these compounds. The instant compounds are particularly active against bacteria and bacteria-like microorganisms. They are therefore suitable for use in human and veterinary medicine, for the prophylaxis and chemotherapy of local and systemic infections caused by these pathogens.

As an illustrative, but not limiting, list of pathogens, the following pathogenic microorganisms are possible targets of the compounds of the present invention. Micrococcaceae, such as *Staphylococci*, for example *Staphylococcus aureus*, *Staph. Epidermidis* and *Staph. Aerogenes*; Lactobacteriaceae, such as *Streptococci*, for example *Streptococcus pyogenes*; Neisseriaceae, such as *Neisseriae*, for example *Neisseria gonorrhoeae* (*Gonococci*); Corynebacteriaceae, such as *Corynebacteria*; *Listeria* bacteria; *Erysipelothrix* bacteria; *Kurthia* bacteria; Enterobacteriaceae, such as *Escherichia* bacteria of the *Coli* group; *Klebsiella* bacteria; *Erwiniae*; *Serratia*; Proteae bacteria; *Providencia* bacteria; *Salmonella* bacteria; *Shigella*; Pseudomonadaceae; *Aeromonas* bacteria; Spirillaceae, such as *Vibrio* bacteria; *Spirillum* bacteria; Parvobacteriaseae; *Brucella* bacteria; *Bordetella* bacteria; *Moraxella* bacteria; *Fusiform* bacteria; Bacillaceae; *Clostridia*; Spirochaetaceae; *Treponema* bacteria; and *Leptospira* bacteria.

Examples which may be cited of diseases which can be prevented, alleviated, or cured by the compounds of the present invention are: diseases of the respiratory passages and of the pharyngeal cavity; otitis; pharyngitis; pneumonia; peritonitis; pyelonephritis; cystitis; endocarditis; systemic infections; and bronchitis.

The compounds of the present invention include all hydrates and salts that can be prepared by those of skill in the art. Under conditions where the compounds of the present invention are sufficiently basic or acidic to form stable non-toxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion.

Alkali metal (for example, sodium, potassium or lithium) or alkaline earth metal (for example calcium) salts of carboxylic acids can also be made.

The compounds of the present invention can be formulated as pharmaceutical compositions and administered to a patient, such as a human patient, in a variety of forms adapted to the chosen route of administration, i.e., orally or parenterally, by intravenous, intramuscular, topical, or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water or other suitable solvent, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient presenting the previously sterile-filtered solutions.

For topical administration, the present compounds may be applied in pure-form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from adsorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the compounds of formula I to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art (U.S. Pat. No. 4,938,949 (Borch et al.)).

Generally, the concentration of the compound(s) of formula (I) in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

Accordingly, the invention includes a pharmaceutical composition comprising a compound of the present invention as described above; or a pharmaceutically acceptable salt thereof, in combination with a pharmaceutically acceptable carrier. Pharmaceutical compositions adapted for oral, topical or parenteral administration, comprising an amount of one or more compounds effective to treat a bacterial infection, are a preferred embodiment of the invention.

The present invention provides a novel class of monocyclic substituted 2-oxazolidinones, specifically termed N-thiolated 2-oxazolidinones as defined herein.

The present invention will therefore be fully understood by one of skill in the art by reference to the following embodiments, examples, and claims.

EXAMPLE 1

In accordance with the present invention, a representative selection of differentially substituted N-thiolated 2-oxazolidinones 1-9 was prepared for antimicrobial screening by N-thiolation of the corresponding 2-oxazolidinones using protocols that have been previously reported by Miller and co-workers (Woulfe, S. R. et al., *Tetrahedron Lett.* 1985, 26, 3891) for β-lactams. The structures of the compounds were confirmed by $^1$H and $^{13}$C NMR spectroscopy, and antibacterial assays were performed by Kirby-Bauer disk diffusion on agar plates according to NCCLS guidelines. (NCCLS (National Committee for Clinical Laboratory Standards) *Methods for Dilution of Antimicrobial Susceptibility Tests for Bacteria that Grow Aerobically*. NCCLS Document M7-A4, Vol. 17, No. 2, 1997) These assays tested both an ATCC strain of methicillin-susceptible *S. aureus* as well as 10 strains of methicillin-resistant *S. aureus* obtained either from ATCC sources or as clinical isolates from a local hospital. The zones of growth inhibition produced by the compounds against each of these microbes after 24 h of incubation are presented in Table 1. Compound susceptibility measurements obtained from agar disk diffusion of oxazolidinones 1-9 against a methicillin-susceptible strain of *Staphylococcus aureus* (*S. aureus* ATCC 25923) and 10 strains of methicillin-resistant *S. aureus*

TABLE 1

| Bacterial strains | Lac | 1 | 2 | 3 | 4 | 5 | 6 | 7 | 8 | 9 | Pen G |
|---|---|---|---|---|---|---|---|---|---|---|---|
| *S. aureus* 849 (ATCC 25923) | 25 | 31 | 16 | 17 | 21 | 19 | 30 | 29 | 20 | 21 | 33 |
| MRSA USF919 (ATCC 43300) | — | 32 | 11 | 19 | 20 | 19 | 30 | 28 | 21 | 13 | — |
| MRSA USF920 (ATCC 33591) | — | 32 | 0 | 19 | 16 | 19 | 28 | 28 | 18 | 15 | — |
| MRSA USF652 | 30 | 30 | 12 | 17 | 16 | 19 | 30 | 30 | 19 | 12 | 8 |
| MRSA USF653 | 30 | 32 | 19 | 20 | 20 | 20 | 31 | 30 | 27 | 25 | 15 |
| MRSA USF654 | 26 | 30 | 14 | 18 | 20 | 22 | 29 | 26 | 23 | 20 | 10 |
| MRSA USF655 | 25 | 30 | 14 | 17 | 20 | 22 | 29 | 28 | 22 | 18 | 14 |
| MRSA USF656 | 28 | 31 | 15 | 19 | 22 | 20 | 31 | 28 | 22 | 20 | 12 |
| MRSA USF657 | 27 | 30 | 12 | 19 | 21 | 22 | 29 | 27 | 22 | 19 | 12 |

TABLE 1-continued

| | (MRSA) | | | | | | | | | | |
|---|---|---|---|---|---|---|---|---|---|---|---|
| Bacterial strains | Lac | 1 | 2 | 3 | 4 | 5 | 6 | 7 | 8 | 9 | Pen G |
| MRSA USF658 | 26 | 31 | 14 | 17 | 18 | 21 | 29 | 27 | 16 | 19 | 19 |
| MRSA USF659 | 24 | 28 | 16 | 19 | 19 | 20 | 26 | 26 | 22 | 22 | 16 |

Figure 2:
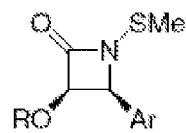
FIG. 2 shows an N-thiolated β-lactam.

The first goal was to determine the effect of substitution at the $C_4$ and $C_5$ centers of the oxazolidinone ring on anti-*Staphylococcus* activity. Accordingly, N-thiolated oxazolidinones 1-5 (as racemates) were examined and compared to two reference compounds, N-methylthio lactam Lac (FIG. 2) and penicillin G.

Compound susceptibility measurements obtained from agar disk diffusion of oxazolidinones 1-9 against a methicillin-susceptible strain of *Staphylococcus aureus* (*S. aureus* ATCC 25923) and 10 strains of methicillin-resistant *S. aureus* (MRSA) In each case, 20 µg of the test compound in $CH_2Cl_2$ was applied to 6 mm cellulose disks prior to inoculation and incubation. The value corresponds to average diameter in mm (triplicate experiments) for the zone of growth inhibitions observed after 24 h of incubation at 37° C. *S. aureus* (ATCC 25923) and methicillin-resistant *S. aureus* (labeled MRSA USF652-659 and USF919-920) were obtained from Lakeland Regional Medical Center, Lakeland, Fla. Lac is the N-thiolated β-lactam shown in FIG. 2. Pen G is penicillin G (potassium salt). Error values are within ±1 mm.

In almost every case, the five oxazolidinones displayed about equal activity against both *S. aureus* and MRSA, as did the corresponding β-lactam (Lac), and were uniformly much more effective than penicillin G (Pen G) against the MRSA strains. The most potent of these five oxazolidinones, compound 1, produced zones of similar dimensions against *S. aureus* to that of penicillin G. Oxazolidinone 2, on the other hand, showed much more moderate activity against both *S. aureus* and MRSA. Mono-substituted oxazolidinones 3-5 also possessed strong anti-MRSA activity, surpassing disubstituted derivative 2, indicating that substituents can be placed at either the $C_4$ or $C_5$ centers, or at both, without significantly affecting bioactivity. This stands in contrast to previous observations from studies of mono-versus disubstituted N-thiolated β-lactams, in which disubstitution on the ring provides for the best anti-MRSA properties. Additionally, replacement of the N-methylthio moiety of compound 4 for N-sec-butylthio (compound 5) leads to no significant improvement in anti-MRSA activity.

Figure 3:
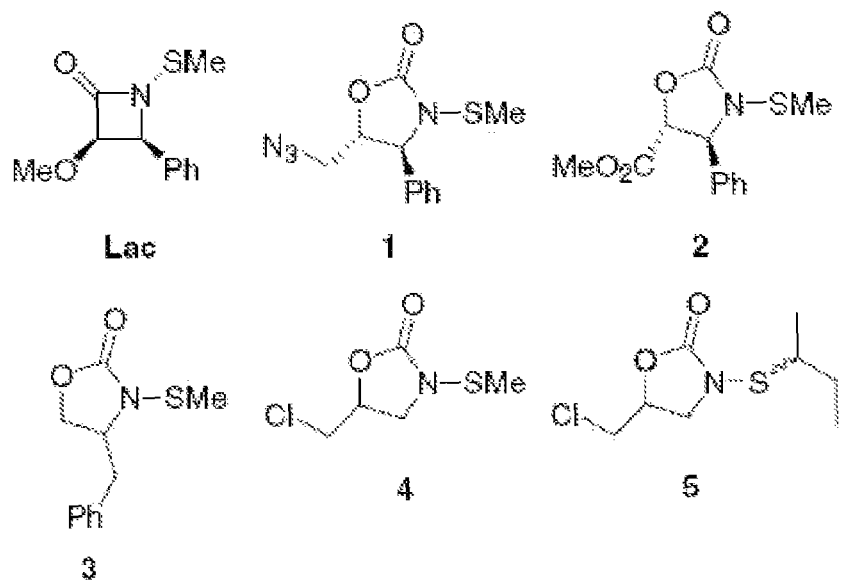
FIG. 3 shows a reference N-thiolated β-lactam (Lac) and N-alkylthio 2-oxazolidinones 1-5.
Figure 4:
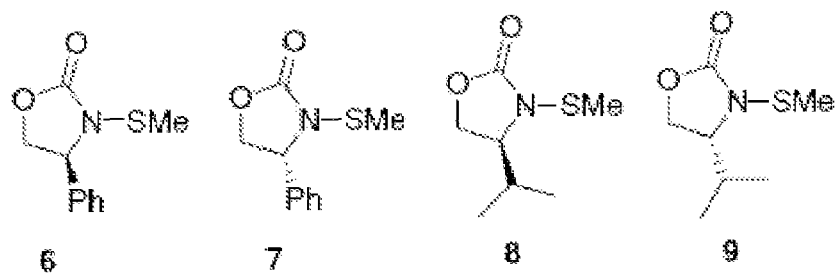
FIG. 4 shows enantiomerically pure N-methylthio 2-oxazolidinones 6-9.

Enantiomerically paired oxazolidinones 6, 7 and 8, 9 were then evaluated for anti-MRSA properties to probe whether absolute stereochemistry was a determinant of activity (FIG. 3). These four compounds were individually prepared from their commercially available N-protio precursors and subjected to Kirby-Bauer testing. First, from these assays, it was noted that the phenyl-substituted oxazolidinones 6 and 7 afforded somewhat larger inhibition zones than the isopropyl-bearing oxazolidinones 8 and 9, indicating stronger anti-MRSA activity. Indeed, oxazolidinone 7 exhibited a lower broth MIC value (8 µg/mL) against both *S. aureus* and MRSA than that of oxazolidinone 8 (16 µg/mL). Second, the S enantiomer in each case was found, on average, to be slightly more active than the R-isomer. Indeed, the growth inhibition zones for R-configured compound 9 were visibly not as clear as they were for the S-stereoisomer 8, indicative of incomplete growth inhibition. Thus, there may be a small but discernible difference in bioactivities of the two enantiomeric forms, which should be further evaluated.

Next, the antibacterial capabilities of the oxazolidinones were examined against *Bacillus anthracis*, the causative agent of anthrax infections, and six other species of *Bacillus*. Concerns about the possible use of *B. anthracis* as a biological weapon have led to widespread efforts to develop antibiotics and vaccines for anthrax infections. For this initial examination, N-thiolated 2-oxazolidinones 6-9 were chosen for Kirby-Bauer testing. The data shown in Table 2 indicate that each of the N-methylthio 2-oxazolidinones inhibits the growth of all seven species of *Bacillus*. Of these four optically pure compounds, however, 6 and 7 had identical activity, while the R compound 9 possessed much weaker and more sporadic activity compared to that of the S-enantiomer 8. The reasons for this seemingly anomalous, but reproducible, difference in bioactivity are still under investigation.

TABLE 2

| *Bacillus* species | 6 | 7 | 8 | 9 |
|---|---|---|---|---|
| B. anthracis | 23 | 23 | 23 | 15 |
| B. globigii | 15 | 17 | 15 | 17 |
| B. thurigensis | 17 | 15 | 16 | 0 |
| B. megaterium | 18 | 20 | 18 | 10 |
| B. subtilus | 19 | 19 | 17 | 19 |
| B. cereus | 24 | 23 | 22 | 15 |
| B. coagulans | 17 | 17 | 17 | 0 |

Compound susceptibility measurements obtained from agar disk diffusion of oxazolidinones 6-9 against *Bacillus anthracis* (Sterne strain) and six other strains of *Bacillus*

In each case, 20 µg of the test compound in $CH_2Cl_2$ was applied to 6 mm cellulose disks prior to inoculation and incubation. The value corresponds to average diameter in mm (triplicate experiments) for the zone of growth inhibitions observed after 24 h of incubation at 37° C. Error values of these measurements are ±1 mm.

As previously described for N-thiolated β-lactams, the antibacterial activity of these agents shows only a small dependence on the ring substituents, but requires the N-alkylthio group. In each case, N-thiolated 2-oxazolidinones exhibited antibacterial activity, whereas the corresponding N-protio oxazolidinones have no antibacterial activity. It is therefore tentatively postulated that these N-thiolated oxazolidinones, like their β-lactam counterparts, react covalently with their biological target through transfer of the organothio side chain as shown in Reaction 1.

Reaction 1

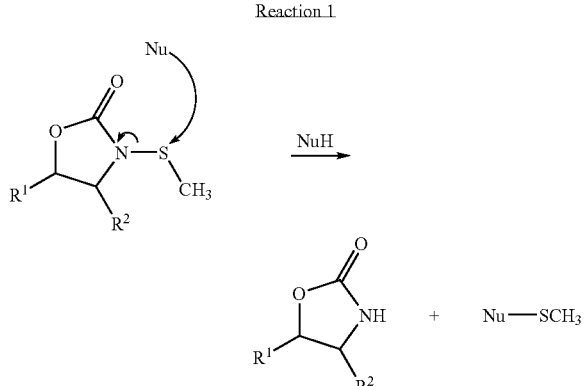

EXAMPLE 2

Development and Characterization of N-thiolated 2-oxazolidinones

Procedure for the Synthesis of N-methylthiolated 2-oxazolidinones

Scheme 1:

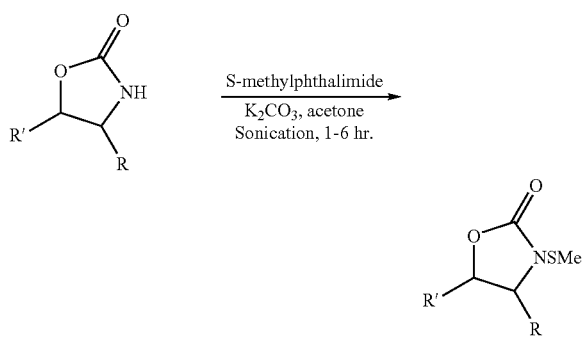

General Procedure of N-methylthiolation of 2-oazolidinones

A mixture of oxazolidinone (1.0 eq), S-methylphthalimide (1.5 eq) and potassium carbonate (1.5 eq) in acetone was sonicated till the reaction was complete. The reaction mixture was diluted with methylene chloride and filtered through celite. The solvent was removed under vacuum and the crude product was purified by column chromatography.

4S-(+)-N-methylthio-4-phenyl-2-oxazolidinone (1a)

Isolated 22 mg (34%) as a colorless oil. $^1$H NMR (CDCl$_3$) δ 7.42-7.24 (m, 5H); 4.80 (t, J=7 Hz, 1H); 4.62 (t, J=8.8 Hz, 1H); 4.22 (dd, J=7.0, 8.8 Hz, 1H); 2.17 (s, 3H). $^{13}$C NMR (CDCl$_3$): δ 138.27, 129.82, 129.67, 127.91, 70.16, 63.79, 21.20.

4R-(−)-N-methylthio-4-phenyl-2-oxazolidinone (2a)

Isolated 62 mg (48%) as a colorless oil. $^1$H NMR (CDCl$_3$) δ 7.42-7.24 (m, 5H); 4.80 (t, J=7 Hz, 1H); 4.62 (t, J=8.8 Hz, 1H); 4.22 (dd, J=7.0, 8.8 Hz, 1H); 2.17 (s, 3H). $^{13}$C NMR (CDCl$_3$) δ 159.08, 138.28, 129.80, 129.65, 127.91, 70.17, 63.75, 21.18.

4S-(−)-N-methylthio-4-isopropyll-2-oxazolidinone (3a)

Isolated as colorless oil. $^1$H NMR (CDCl$_3$) δ 4.24 (t, J=9 Hz, 1H); 4.06 (dd, J=9 Hz, 6 Hz, 1H); 3.78-3.71 (m, 1H); d 2.42 (s, 3H); 2.30-2.22 (m, 1H); 0.91 (d, J=7.8 Hz, 3H); 0.84 (d, J=6.8 Hz, 3H). $^{13}$C NMR (CDCl$_3$) δ159.12, 63.38, 62.32, 28.15, 20.73, 17.53, 14.12

4R-(+)-N-methylthio-4-isopropyl-2-oxazolidinone (4a)

Isolated as colorless oil. $^1$H NMR (CDCl$_3$) δ 4.24 (t, J=9 Hz, 1H); 4.06 (dd, J=9 Hz, 6 Hz, 1H); 3.78-3.71 (m, 1H); 2.42 (s, 3H); 2.30-2.22 (m, 1H); 0.91 (d, J=7.8 Hz, 3H); 0.84 (d, J=6.8 Hz, 3H). $^{13}$C NMR (CDCl$_3$) δ159.12, 63.38, 62.32, 28.15, 20.73, 17.53, 14.12

Additional Studies Detailing Kirby-Bauer Zones of Inhibition of N-methylthio and N—H Oxazolidinones.

TABLE 3

| Compound | R | R' | X | MRSA (inhibition)[a] | S. aureus (Inhibition)[b] |
|---|---|---|---|---|---|
| 1 | S-Phenyl | H | H | 0 | 0 |
| 1a | S-Phenyl | H | SMe | 29 | 30 |
| 2 | R-Phenyl | H | H | 0 | 0 |
| 2a | R-Phenyl | H | SMe | 28 | 29 |
| 3 | S-iPropyl | H | H | 0 | 0 |
| 3a | S-iPropyl | H | SMe | 16[c] | 20[c] |
| 4 | R-iPropyl | H | H | 0 | 0 |
| 4a | R-iPropyl | H | SMe | 19[c] | 21[c] |

[a]Reported as median diameter of zone of inhibition, in mm of 10 strains of MRSA (652-659, 919-920)
[b]Median zone of inhibition for *S. Aureaus* strain 849.
[c]partial inhibition within this diameter.

The disclosure of all publications cited above are expressly incorporated herein by reference, each in its entirety, to the same extent as if each were incorporated by reference individually.

While the invention has been described in terms of various preferred embodiments, those skilled in the art will recognize that various modifications, substitutions, omissions, and changes may be made without departing from the spirit of the present invention. Accordingly, it is intended that the scope of the present invention be limited solely by the scope of the following claims.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of treating bacterial infection comprising administering an effective amount of a N-thiolated-2-oxazolidinone selected from the group consisting of

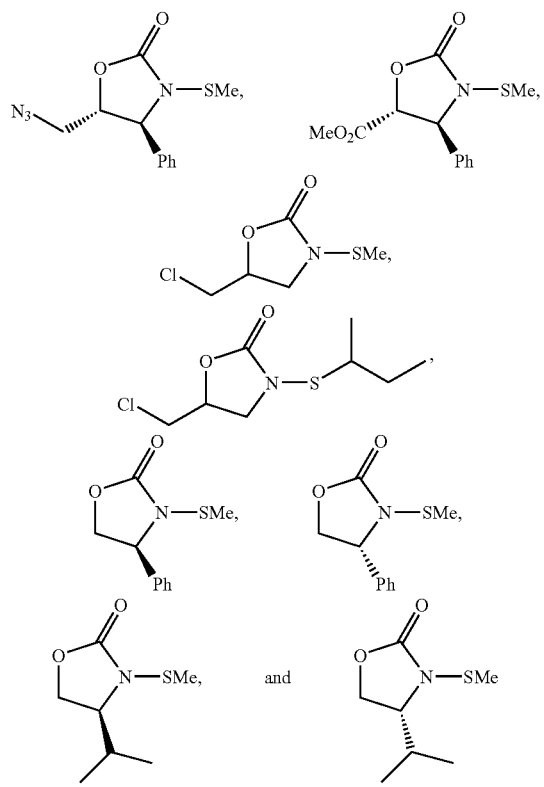

to a patient in need thereof.

2. The method of claim 1, wherein the bacterium is a *Staphylococcus*.

3. The method of claim 1, wherein the *Staphylococcus* is a methicillin-resistant *Staphylococcus*.

4. The method of claim 3, wherein said methicillin-resistant *Staphylococcus* is selected from the group consisting of MRSA USF919, MRSA USF920, MRSA USF652, MRSA USF653, MRSA USF654, MRSA USF655, MRSA USF656, MRSA USF657, MRSA USF658 and MRSA USF659.

5. The method of claim 1 wherein the bacterium is a *Bacillus*.

6. The method of claim 5 wherein the *Bacillus* spp. is selected from the group consisting of *B. anthracis, B. globigii, B. thurigensis, B. megaterium, B. subtilis, B. cereus* and *B. coagulans*.

7. The method of claim 1 wherein the N-thiolated 2-oxazolidinone compound is administered in a pharmaceutically acceptable carrier.

8. A method of inhibiting growth of a bacterium comprising the step of administering an effective amount of an N-thiolated 2-oxazolidinone compound selected from the group consisting of,

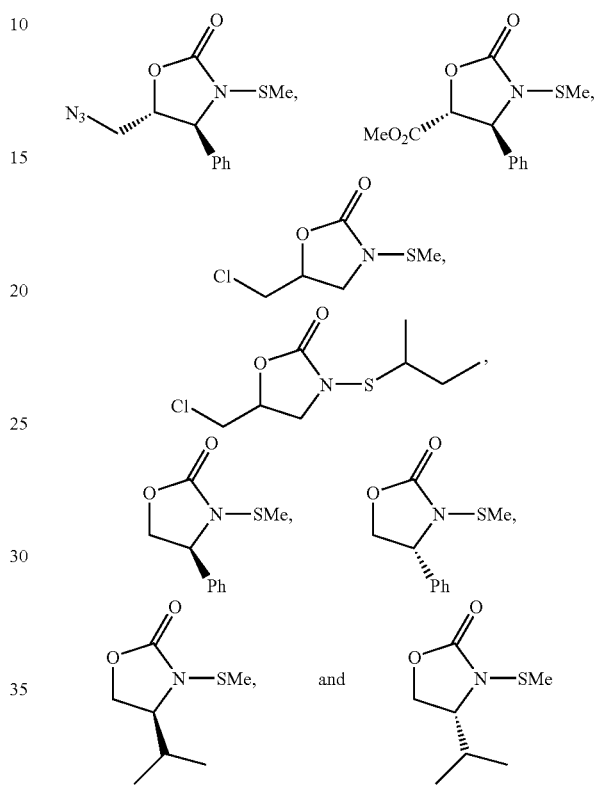

or a salt or hydrate thereof, to the bacterium.

9. The method of claim 8 wherein the bacterium is a *Staphylococcus*.

10. The method of claim 1, wherein the *Staphylococcus* is a methicillin-resistant *Staphylococcus*.

11. The method of claim 3, wherein said methicillin-resistant *Staphylococcus* is selected from the group consisting of MRSA USF919, MRSA USF920, MRSA USF652, MRSA USF653, MRSA USF654, MRSA USF655, MRSA USF656, MRSA USF657, MRSA USF658 and MRSA USF659.

12. The method of claim 1 wherein the bacterium is a *Bacillus*.

13. The method of claim 5 wherein the *Bacillus* is selected from the group consisting of *B. anthracis, B. globigii, B. thurigensis, B. megaterium, B. subtilis, B. cereus* and *B. coagulans*.

* * * * *